US 7,799,094 B2

(12) United States Patent
Huet et al.

(10) Patent No.: US 7,799,094 B2
(45) Date of Patent: *Sep. 21, 2010

(54) OXIDATION DYE COMPOSITION COMPRISING A CATIONIC SURFACTANT, A BIOHETEROPOLYSACCHARIDE, AN AMPHOTERIC SURFACTANT AND A DYE PRECURSOR

(75) Inventors: Nathalie Huet, Paris (FR); Marie-Pascale Audousset, Asnieres (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/000,890

(22) Filed: Dec. 18, 2007

(65) Prior Publication Data

US 2009/0000041 A1    Jan. 1, 2009

Related U.S. Application Data

(60) Provisional application No. 60/881,148, filed on Jan. 19, 2007.

(30) Foreign Application Priority Data

Dec. 21, 2006    (FR) .................................. 06 55806

(51) Int. Cl.
*A61Q 5/10* (2006.01)
(52) U.S. Cl. ...................... 8/405; 8/406; 8/552; 8/594; 8/606
(58) Field of Classification Search ....................... 8/405, 8/406, 552, 594, 606
See application file for complete search history.

(56) References Cited

U.S. PATENT DOCUMENTS

| | | | |
|---|---|---|---|
| 2,528,378 A | 10/1950 | Mannheimer et al. | |
| 2,781,354 A | 2/1957 | Mannheimer et al. | |
| 4,137,180 A | 1/1979 | Naik et al. | |
| 4,834,768 A | 5/1989 | Grollier | |
| 4,874,554 A | 10/1989 | Lange et al. | |
| 4,904,275 A * | 2/1990 | Grollier | 8/408 |
| 5,061,289 A | 10/1991 | Clausen et al. | |
| 5,196,029 A | 3/1993 | Kawase et al. | |
| 5,380,340 A | 1/1995 | Neunhoeffer et al. | |
| 5,708,151 A | 1/1998 | Möckli | |
| 5,766,576 A | 6/1998 | Löwe et al. | |
| 6,099,592 A | 8/2000 | Vidal et al. | |
| 6,099,593 A | 8/2000 | Terranova et al. | |
| 6,270,533 B1 | 8/2001 | Genet et al. | |
| 6,340,371 B1 | 1/2002 | Genet et al. | |
| 6,377,398 B1 | 4/2002 | Pieri et al. | |
| 6,565,614 B1 | 5/2003 | Genet et al. | |
| 6,638,321 B1 | 10/2003 | Genet et al. | |
| 6,660,046 B1 | 12/2003 | Terranova et al. | |
| 6,730,789 B1 | 5/2004 | Birault et al. | |
| 6,783,557 B1 | 8/2004 | Terranova et al. | |
| 7,402,180 B2 | 7/2008 | Vuarier et al. | |
| 2003/0150069 A1 | 8/2003 | Kleen et al. | |
| 2004/0025266 A1 * | 2/2004 | Cottard et al. | 8/405 |
| 2004/0187227 A1 * | 9/2004 | Lagrange | 8/405 |

FOREIGN PATENT DOCUMENTS

| | | |
|---|---|---|
| DE | 2 359 399 A1 | 6/1975 |
| DE | 3 843 892 A1 | 6/1990 |
| DE | 4 133 957 A1 | 4/1993 |
| DE | 195 43 988 A1 | 5/1997 |
| DE | 200 11 145 U1 | 10/2001 |
| EP | 0 714 954 A2 | 6/1996 |
| EP | 0 770 375 A1 | 5/1997 |
| EP | 1 142 561 A1 | 10/2001 |
| EP | 1 224 927 A1 | 7/2002 |
| EP | 1 234 569 A1 | 8/2002 |
| EP | 1 279 395 A1 | 1/2003 |
| EP | 1 348 695 A1 | 10/2003 |
| EP | 1 559 403 A1 | 8/2005 |
| EP | 1 716 841 A1 | 11/2006 |
| EP | 1 820 491 A1 | 8/2007 |
| FR | 2 548 895 A1 | 1/1985 |
| FR | 2 575 067 A1 | 6/1986 |
| FR | 2 733 749 A1 | 11/1996 |
| FR | 2 750 048 A1 | 12/1997 |
| FR | 2 766 177 A1 | 1/1999 |
| FR | 2 766 178 A1 | 1/1999 |
| FR | 2 766 179 A1 | 1/1999 |
| FR | 2 782 716 A1 | 3/2000 |
| FR | 2 782 718 A1 | 3/2000 |
| FR | 2 782 719 A1 | 3/2000 |
| FR | 2 788 521 A1 | 7/2000 |
| FR | 2 788 522 A1 | 7/2000 |

(Continued)

OTHER PUBLICATIONS

"Handbook of Surfactants" by M.R. Porter, published by Blackie & Son (Glasgow and London), 1991, pp. 116-178).
English language Derwent abstract for DE 2359399 A1, (1975).
English language Derwent abstract for DE 200 11 145 U1, (2001).
English language Derwent abstract for EP 0770375 A1, (1997).
English language Derwent abstract for EP 1224927 A1, (2002).
English language Derwent abstract for EP 1348695 A1, (2003).
English language Derwent abstract for EP 1716841 A1, (2005).
English language Derwent abstract for FR 2782716 A1, (2000).

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present invention relates to a composition for dyeing keratin fibers, comprising at least one dye precursor, at least one bioheteropolysaccharide, at least one cationic surfactant and at least one amphoteric surfactant.

Such a composition affords improved ease of application and also improved dyeing properties.

19 Claims, No Drawings

FOREIGN PATENT DOCUMENTS

| | | |
|---|---|---|
| FR | 2 801 308 A1 | 5/2001 |
| FR | 2 837 821 A1 | 10/2003 |
| GB | 1 026 978 | 4/1966 |
| GB | 1 153 196 | 5/1969 |
| JP | 2-19576 A | 1/1990 |
| JP | 5-163124 | 6/1993 |
| JP | 2526099 | 8/1996 |
| WO | WO 94/08969 A1 | 4/1994 |
| WO | WO 94/08970 A1 | 4/1994 |
| WO | WO 95/01772 A1 | 1/1995 |
| WO | WO 95/15144 A1 | 6/1995 |
| WO | WO 96/15765 A1 | 5/1996 |
| WO | WO 01/78668 A1 | 10/2001 |

OTHER PUBLICATIONS

English language Derwent abstract for FR 2837821 A1, (2003).
English language Derwent abstract for JP 2-19576 A, (1990).
English language Derwent abstract for JP 2526099, (1996).
English language Derwent abstract for JP 5-163124, (1993).
English language abstract for WO 94/08969 A1, (1994).
English language abstract for WO 94/08970 A1, (1994).
English language abstract for WO 96/15765 A1, (1996).
English language abstract for WO 01/78668 A1, (2001).
Co-Pending U.S. Appl. No. 12/003,329; Title: Direct Dye Composition Comprising a Cationic Surfactant, A Bioheteropolysaccharide, an Amphoteric Surfactant, and a Direct Dye; U.S. Filing Date: Dec. 21, 2007.
Office Action in co-pending U.S. Appl. No. 12/000,890, dated Nov. 25, 2008.
French Search Report for French Application No. 0655806 (French priority application for the present application) dated Sep. 7, 2007.
French Search Repot for French Application No. 0655808 (French priority application for U.S. Appl. No. 12/003,329) dated Sep. 10, 2007.
Final Office Action dated Jun. 29, 2009, in co-pending U.S. Appl. No. 12/003,329.
Notice of Allowance dated Nov. 2, 2009, in co-pending U.S. Appl. No. 12/003,329.

* cited by examiner

OXIDATION DYE COMPOSITION COMPRISING A CATIONIC SURFACTANT, A BIOHETEROPOLYSACCHARIDE, AN AMPHOTERIC SURFACTANT AND A DYE PRECURSOR

The present invention relates to a composition for the oxidation dyeing of keratin fibers, in particular human keratin fibers.

It is known practice to dye keratin fibers, and in particular human hair, with dye compositions containing oxidation dye precursors, which are generally known as oxidation bases, such as ortho- or para-phenylenediamines, ortho- or para-aminophenols and heterocyclic couplers. These oxidation bases are colorless or weakly colored compounds which, when combined with oxidizing products, can give rise to colored compounds via a process of oxidative condensation.

It is also known that the shades obtained with these oxidation bases can be varied by combining them with couplers or coloration modifiers, these agents being chosen especially from aromatic meta-diamines, meta-aminophenols, meta-diphenols and certain heterocyclic compounds such as indole compounds.

The variety of molecules used as oxidation bases and couplers allows a wide range of colors to be obtained.

The "permanent" coloration obtained by means of these oxidation dyes must moreover satisfy a certain number of requirements. Thus, it must have no toxicological drawback, it must allow shades to be obtained in the desired strength, and it must show good fastness with respect to external agents such as light, bad weather, washing, permanent-waving, perspiration and rubbing.

The dyes must also allow gray hair to be covered and, finally, they must be as unselective as possible, i.e. they must produce the smallest possible differences in coloration along the same keratin fiber, which is generally differently sensitized (i.e. damaged) between its end and its root.

It is already known practice to combine these dye precursors with bioheteropolysaccharides. Patent application FR 2 575 067 especially describes compositions for dyeing keratin fibers, comprising an oxidation dye and a bioheteropolysaccharide, for improving the fastness of the shades, with good coverage of gray hair and a reduction in selectivity, this composition possibly containing surfactants.

However, these compositions do not give entirely satisfactory dyeing properties, especially as regards the selectivity. Moreover, the texture of the products is not entirely satisfactory, which is detrimental to the working qualities of the product such as the ease of mixing with the oxidizing agents and/or the ease of application of the mixtures to keratin fibers.

Thus, the aim of the present invention is to develop novel compositions for the oxidation dyeing of keratin fibers such as the hair, which allow these technical problems to be solved. In particular, the invention seeks to obtain compositions that can afford products which apply well to keratin fibers and which have improved dyeing properties.

Thus, this aim is achieved with the present invention, one subject of which is a composition for dyeing keratin fibers, comprising at least one dye precursor, at least one bioheteropolysaccharide, at least one cationic surfactant and at least one amphoteric surfactant.

Such a composition in particular affords improved ease of application and also improved dyeing properties, in particular as regards the selectivity, which shows an improvement in the uniformity of coloration over the length of the locks.

The composition of the invention may contain as dye precursor an oxidation base and/or a coupler. According to one particular embodiment, the composition comprises at least one oxidation base.

By way of example, the oxidation base(s) is (are) chosen from para-phenylenediamines, bis(phenyl)-alkylenediamines, para-aminophenols, bis-para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloro-aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxy-ethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetyl-aminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)-pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylamino-ethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxy-ethyl)amino-3-amino-6-methoxypyridine and 3,4-diaminopyridine, and the addition salts thereof with an acid.

Other pyridine oxidation bases that are useful in the present invention are the 3-aminopyrazolo[1,5-a]-pyridine oxidation bases or addition salts thereof described, for example, in patent application FR 2 801 308. Examples that may be mentioned include pyrazolo[1,5-a]pyrid-3-ylamine, 2-acetylaminopyrazolo-[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-yl-pyrazolo[1,5-a]pyrid-3-ylamine, pyrazol[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-amino-pyrazolo[1,5-a]pyridin-5-ol, 3-aminopyrazolo[1,5-a]-pyridin-4-ol, 3-aminopyrazolo[1,5-a]pyridin-6-ol and 3-aminopyrazolo[1,5-a]pyridin-7-ol, and the addition salts thereof with an acid or with a base.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)-amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolyl-propylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The oxidation base(s) that is (are) useful may be cationic oxidation bases. The term "cationic oxidation base" means a base that bears at least one permanent cationic charge.

The cationic oxidation bases that may be used according to the invention may be para-phenylenediamines as described especially in patent applications FR 2 766 177 and FR 2 766 178, para-aminophenols as described, for example, in patent applications FR 2 766 177 and FR 2 766 178, ortho-phenylenediamines as described, for example, in patent applications FR 2 782 718, FR 2 782 716 and FR 2 782 719, and cationic ortho-aminophenols or heterocyclic bases or double bases more particularly as described in patent application FR 2 766 179. Examples that may especially be mentioned include cationic oxidation bases of para-phenylenediamine structure, one of the amine functions of which is a tertiary amine, bearing a pyrrolidine nucleus, the molecule containing at least one quaternized nitrogen atom. Bases of this type are described in document FR 2 837 821.

Cationic heterocyclic bases that may be mentioned include cationic pyrazole bases or cationic pyrazolopyrimidines, for example described in documents FR 2 788 521 and FR 2 788 522.

The oxidation base(s) present in the composition of the invention is (are) each generally present in an amount of between 0.001% and 10% by weight approximately, and preferably between 0.005% and 6%, relative to the total weight of the dye composition.

Among the coupler(s) that may especially be mentioned are meta-phenylenediamines, meta-aminophenols, meta-diphenols, naphthalene-based couplers and heterocyclic couplers, and the addition salts thereof.

The meta-aminophenol(s) that may be used as coupler in the ready-to-use dye composition in accordance with the invention is (are) preferably chosen from the compounds of formula (I) below, and the addition salts thereof with an acid:

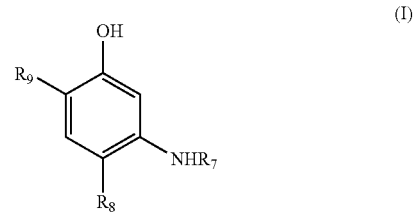

(I)

in which:
  $R_7$ represents a hydrogen atom or a $C_1$-$C_4$ alkyl, $C_1$-$C_4$ monohydroxyalkyl or $C_2$-$C_4$ polyhydroxyalkyl radical,
  $R_8$ represents a hydrogen atom, a $C_1$-$C_4$ alkyl or $C_1$-$C_4$ alkoxy radical or a halogen atom chosen from chlorine, bromine and fluorine, $R_9$ represents a hydrogen atom or a $C_1$-$C_4$ alkyl, $C_1$-$C_4$ alkoxy, $C_1$-$C_4$ monohydroxyalkyl, $C_2$-$C_4$ polyhydroxyalkyl, $C_1$-$C_4$ monohydroxyalkoxy or $C_2$-$C_4$ polyhydroxyalkoxy radical.

Among the meta-aminophenols of formula (I) above, mention may be made more particularly of meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol and 5-(γ-hydroxy-propylamino)-2-methylphenol, and the addition salts thereof with an acid.

Other useful couplers are, for example, couplers among the substituted naphthalenes of formula (II) below, and the addition salts thereof with an acid:

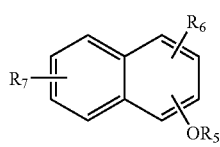

(II)

in which:
R$_5$ represents a hydrogen atom or a group —CO—R in which R represents a $C_1$-$C_4$ alkyl radical;
R$_6$ represents a hydrogen atom, a hydroxyl or $C_1$-$C_4$ alkyl radical, or a group —SO$_3$H;
R$_7$ represents a hydrogen atom or a hydroxyl radical; it being understood that at least one of the radicals R$_5$ to R$_7$ is other than a hydrogen atom.

Among the substituted naphthalenes of formula (II) that may be used as coupler in the dye compositions in accordance with the invention, mention may be made especially of:
1,7-dihydroxynaphthalene,
2,7-dihydroxynaphthalene,
2,5-dihydroxynaphthalene,
2,3-dihydroxynaphthalene,
1-acetoxy 2-methylnaphthalene,
1-hydroxy 2-methylnaphthalene,
1-hydroxy 4-naphthalenesulfonic acid, and the addition salts thereof with an acid.

The meta-phenylenediamine(s) that may be used as coupler in the ready-to-use dye composition in accordance with the invention is (are) preferably chosen from the compounds of formula (III) below, and the addition salts thereof with an acid:

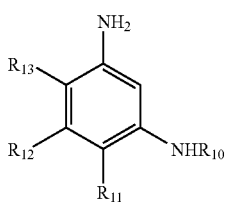

(III)

in which:
R$_{10}$ represents a hydrogen atom or a $C_1$-$C_4$ alkyl, $C_1$-$C_4$ monohydroxyalkyl or $C_2$-$C_4$ polyhydroxyalkyl radical;
R$_{11}$ and R$_{12}$, which may be identical or different, represent a hydrogen atom or a $C_1$-$C_4$ alkyl, $C_1$-$C_4$ monohydroxyalkoxy or $C_2$-$C_4$ polyhydroxyalkoxy radical;

R$_{13}$ represents a hydrogen atom, a $C_1$-$C_4$ alkoxy, $C_1$-$C_4$ aminoalkoxy, $C_1$-$C_4$ monohydroxyalkoxy or $C_2$-$C_4$ polyhydroxyalkoxy radical or a 2,4-diaminophenoxyalkoxy radical.

Among the meta-phenylenediamines of formula (III) above, mention may be made more particularly of 2,4-diaminobenzene, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis-(2,4-diaminophenoxy)methane, 1-(β-aminoethyloxy)-2,4-diaminobenzene, 2-amino-1-(β-hydroxyethyloxy)-4-methyl-aminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene and 2-amino-4-N-(β-hydroxyethyl)amino-1-methoxybenzene, and the addition salts thereof with an acid.

The meta-diphenol(s) that may be used as coupler in the ready-to-use dye composition in accordance with the invention is (are) preferably chosen from the compounds of formula (IV) below, and the addition salts thereof with an acid:

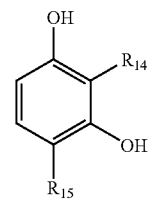

(IV)

in which:
R$_{14}$ and R$_{15}$, which may be identical or different, represent a hydrogen atom, a $C_1$-$C_4$ alkyl radical or a halogen atom chosen from chlorine, bromine and fluorine.

Among the meta-diphenols of formula (IV) above, mention may be made more particularly of 1,3-dihydroxybenzene, 2-methyl-1,3-dihydroxybenzene, 4-chloro-1,3-dihydroxybenzene and 2-chloro-1,3-dihydroxybenzene, and the addition salts thereof with an acid.

In the composition of the present invention, the coupler(s) is (are) each generally present in an amount of between 0.001% and 10%, and preferably between 0.005% and 6% by weight approximately, relative to the total weight of the dye composition.

In general, the addition salts of the oxidation bases and of the couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

For the purposes of the present invention, the term "bio-heteropolysaccharides" in particular means substances synthesized via fermentation of sugars by microorganisms. Bio-heteropolysaccharides in particular often contain units chosen from mannose, glucose and glucuronic acid or galacturonic acid units in their chain, these units being optionally acylated.

Mention may be made especially of the xanthan gums produced by the bacterium *Xanthomonas campestri* and mutants and variants thereof.

These xanthan gums generally have a molecular weight of between 1 000 000 and 50 000 000.

Mention may also be made of the scleroglucans gums produced by *Sclerotium rolfsii*, the gellan gums produced by

*Pseudomonas elodea* or *Sphingomonias*, the pullulan gums produced by *Aureobacidium pullulens*, the Curdlar gums produced by alcaligenes of the *Faecalis myxogenes* type, the xanthan produced by numerous organisms, including *Leuconostoc mesenteroides* and *Leuconostoc dextrantum*, the grifolan gums produced by *Grifola frondara*, the lentinan gums produced by *Lentinus edodes*, the schizophyllan gums produced by *Schizophyllum commine*, the spirulinan gums produced by *Spirulina sybsyla* and the krestin gums produced by *Coriates versicolor*.

Xanthan gums and scleroglucan gums are preferably used. Even more preferentially, scleroglucan gums are used.

The bioheteropolysaccharide is generally included in the dye composition in amounts ranging from 0-0.01% to 10% and preferably between 0.1% and 4% by weight relative to the total weight of the composition.

The composition according to the invention comprises one or more cationic surfactants that are well known per se, such as optionally polyoxyalkylenated primary, secondary or tertiary fatty amine salts, and quaternary ammonium salts, and mixtures thereof.

According to the invention, the cationic surfactants are not polymeric, i.e. they are not obtained by polymerization of monomers other than alkylene oxides or by grafting of cationic groups onto existing natural pigments.

Fatty amines that may especially be mentioned include alkylamidoamines, for instance ($C_8$-$C_{30}$)alkylamidodi($C_1$-$C_6$)alkylamines and in particular stearamidopropyl-dimethylamine (Mackine 301 sold by MacIntyre).

Examples of quaternary ammonium salts that may especially be mentioned include:
those having the general formula (V) below:

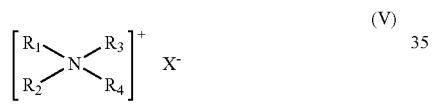

(V)

in which the symbols $R_1$ to $R_4$, which may be identical or different, represent a linear or branched aliphatic radical containing from 1 to 30 carbon atoms or an aromatic radical such as aryl or alkylaryl. The aliphatic radicals may comprise heteroatoms such as, especially, oxygen, nitrogen, sulfur and halogens. The aliphatic radicals are chosen, for example, from ($C_1$-$C_{30}$)alkyl, alkoxy, ($C_2$-$C_6$) polyoxyalkylene, alkylamide, ($C_{12}$-$C_{22}$)alkylamido ($C_2$-$C_6$)alkyl, ($C_{12}$-$C_{22}$)alkyl acetate and hydroxyalkyl radicals, containing from about 1 to 30 carbon atoms; $X^-$ is an anion chosen from the group of halides, phosphates, acetates, lactates, ($C_2$-$C_6$)alkyl sulfates and alkylsulfonates or alkylarylsulfonates;

quaternary ammonium salts of imidazoline, for instance those of formula (VI) below:

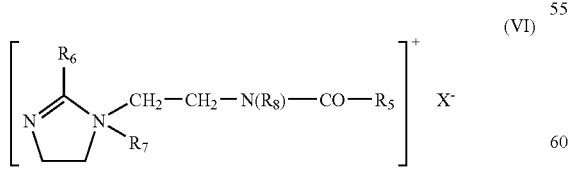

(VI)

in which $R_5$ represents an alkenyl or alkyl radical containing from 8 to 30 carbon atoms, for example fatty acid derivatives of tallow or of coconut, $R_6$ represents a hydrogen atom, a $C_1$-$C_4$ alkyl radical or an alkenyl or alkyl radical containing from 8 to 30 carbon atoms, $R_7$ represents a $C_1$-$C_4$ alkyl radical, $R_8$ represents a hydrogen atom or a $C_1$-$C_4$ alkyl radical, and $X^-$ is an anion chosen from the group of halides, phosphates, acetates, lactates, alkyl sulfates, alkylsulfonates and alkylarylsulfonates. Preferably, $R_5$ and $R_6$ denote a mixture of alkenyl or alkyl radicals containing from 12 to 21 carbon atoms, for example fatty acid derivatives of tallow, $R_7$ denotes methyl and $R_8$ denotes hydrogen. Such a product is, for example, Quaternium-27 (CTFA 2002), Quaternium-87 (CTFA 2002) or Quaternium-83 (CTFA 2002), which are sold under the name "Varisoft®" W575PG by the company Goldschmidt, diquaternary ammonium salts of formula (VII):

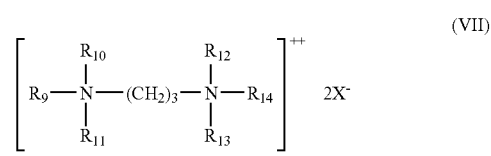

(VII)

in which $R_9$ denotes an aliphatic radical containing from about 16 to 30 carbon atoms, $R_{10}$, $R_{11}$, $R_{12}$, $R_{13}$ and $R_{14}$, which may be identical or different, are chosen from hydrogen and an alkyl radical containing from 1 to 4 carbon atoms, and $X^-$ is an anion chosen from the group of halides, acetates, phosphates, nitrates, ethyl sulfates and methyl sulfates. Such diquaternary ammonium salts in particular comprise propanetallowediammonium dichloride;

quaternary ammonium salts comprising at least one ester function, such as those of formula (VIII) below:

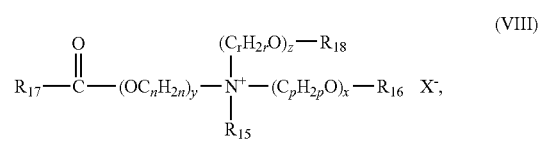

(VIII)

in which:

$R_{15}$ is chosen from $C_1$-$C_6$ alkyl radicals and $C_1$-$C_6$ hydroxyalkyl or dihydroxyalkyl radicals;

$R_{16}$ is chosen from:

a radical

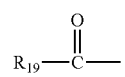

linear or branched, saturated or unsaturated $C_1$-$C_{22}$ hydrocarbon-based radicals $R_{20}$, a hydrogen atom, $R_{17}$ is chosen from:

a radical

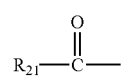

linear or branched, saturated or unsaturated $C_1$-$C_6$ hydrocarbon-based radicals $R_{22}$, a hydrogen atom, $R_{17}$, $R_{19}$ and $R_{21}$, which may be identical or different, are chosen from linear or branched, saturated or unsaturated $C_7$-$C_{21}$ hydrocarbon-based radicals;

r, n and p, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z is from 1 to 15, that when x is 0, then $R_{16}$ denotes $R_{20}$ and that when z is 0, then $R_{18}$ denotes $R_{22}$.

The alkyl radicals $R_{15}$ may be linear or branched, and more particularly linear.

Preferably, $R_{15}$ denotes a methyl, ethyl, hydroxyethyl or dihydroxypropyl radical, and more particularly a methyl or ethyl radical.

Advantageously, the sum x+y+z is from 1 to 10.

When $R_{16}$ is a hydrocarbon-based radical $R_{20}$, it may be long and contain from 12 to 22 carbon atoms, or short and contain from 1 to 3 carbon atoms.

When $R_{18}$ is a hydrocarbon-based radical $R_{22}$, it preferably contains 1 to 3 carbon atoms.

Advantageously, $R_{17}$, $R_{19}$ and $R_{21}$, which may be identical or different, are chosen from linear or branched, saturated or unsaturated $C_{11}$-$C_{21}$ hydrocarbon-based radicals, and more particularly from linear or branched, saturated or unsaturated $C_{11}$-$C_{21}$ alkyl and alkenyl radicals.

Preferably, x and z, which may be identical or different, are 0 or 1.

Advantageously, y is equal to 1.

Preferably, r, n and p, which may be identical or different, are equal to 2 or 3 and even more particularly equal to 2.

The anion $X^-$ is preferably a halide (chloride, bromide or iodide) or a $C_1$-$C_4$ alkyl sulfate, more particularly methyl sulfate. However, methanesulfonate, phosphate, nitrate, tosylate, an anion derived from an organic acid, such as acetate or lactate, or any other anion that is compatible with the ammonium containing an ester function may be used.

The anion $X^-$ is even more particularly chloride or methyl sulfate.

Use is made more particularly in the composition according to the invention of the ammonium salts of formula (IV) in which:

$R_{15}$ denotes a methyl or ethyl radical, x and y are equal to 1;

z is equal to 0 or 1;

r, n and p are equal to 2;

$R_{16}$ is chosen from:

a radical

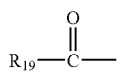

methyl, ethyl or $C_{14}$-$C_{22}$ hydrocarbon-based radicals, a hydrogen atom;

$R_{18}$ is chosen from:

a radical

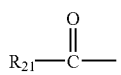

a hydrogen atom;

$R_{17}$, $R_{19}$ and $R_{21}$, which may be identical or different, are chosen from linear or branched, saturated or unsaturated $C_{13}$-$C_{17}$ hydrocarbon-based radicals, and preferably from linear or branched, saturated or unsaturated $C_{13}$-$C_{17}$ alkyl and alkenyl radicals.

The hydrocarbon-based radicals are advantageously linear.

Examples of compounds of formula (VIII) that may be mentioned include the salts (especially chloride or methyl sulfate) of diacyloxyethyldimethylammonium, of diacyloxyethylhydroxyethylmethylammonium, of monoacyloxyethyldihydroxyethylmethylammonium, of triacyloxyethylmethylammonium, of monoacyloxyethylhydroxyethyldimethylammonium, and mixtures thereof. The acyl radicals preferably contain 14 to 18 carbon atoms and are more particularly derived from a plant oil, for instance palm oil or sunflower oil. When the compound contains several acyl radicals, these radicals may be identical or different.

These products are obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart® by the company Cognis, Stepanquat® by the company Stepan, Noxamium® by the company Ceca, and Rewoquat® WE 18 by the company Rewo-Goldschmidt.

The composition according to the invention may preferably contain a mixture of quaternary ammonium mono-, di- and triester salts with a weight majority of diester salts.

Examples of mixtures of ammonium salts that may be used include the mixture containing 15% to 30% by weight of acyloxyethyldihydroxyethylmethylammonium methyl sulfate, 45% to 60% of diacyloxyethylhydroxylethylmethylaammonium methyl sulfate and 15% to 30% of triacyloxyethylmethylammonium methyl sulfate, the acyl radicals containing from 14 to 18 carbon atoms and being derived from optionally partially hydrogenated palm oil.

It is also possible to use the ammonium salts comprising at least one ester function described in U.S. Pat. No. 4,874,554 and U.S. Pat. No. 4,137,180.

Among the quaternary ammonium salts mentioned above that are preferably used are those corresponding to formula (V) or formula (VIII). Mention may especially be made firstly of tetraalkylammonium chlorides, for instance dialkyldimethylammonium or alkyltrimethylammonium chlorides in which the alkyl radical contains from about 12 to 22 carbon atoms, in particular behenyltrimethylammonium, distearyldimethylammonium, cetyltrimethylammonium or benzyldimethylstearylammonium chlorides, or alternatively, secondly, palmitylamidopropyltrimethylammonium chloride or stearamidopropyldimethyl(myristyl acetate)ammonium chloride corresponding to Quaternium-70 (CTFA 2002) sold under the name Ceraphyl®70 by the company ISP.

The cationic surfactants that are particularly preferred in the composition of the invention are chosen from quaternary ammonium salts, and in particular from behenyltrimethylammonium chloride, cetyltrimethylammonium chloride, Quaternium-83, Quaternium-87, behenylamidopropyl-2,3- dihydroxypropyl-dimethylammonium chloride, palmitylamidopropyl-trimethylammonium chloride and stearamidopropyl-dimethylamine.

The composition according to the invention preferably comprises the cationic surfactant(s) in an amount ranging from 0.01% to 10% by weight and preferably from 0.1% to 4% by weight relative to the total weight of the composition.

Preferably, the weight ratio between the cationic surfactant(s)/the biopolysaccharide(s) is greater than 1 and is ideally between 1 and 10.

The amphoteric surfactants contained in the composition of the invention are surfactants that are known per se in the field of the direct dyeing of keratin fibers.

The amphoteric surfactants that are useful in the composition of the invention are known in the art. These amphoteric surfactants may especially be aliphatic secondary or tertiary amine derivatives in which the aliphatic radical is a linear or branched chain containing 8 to 22 carbon atoms and containing at least one water-solubilizing anionic group (for example carboxylate, sulfonate, sulfate, phosphate or phosphonate); mention may also be made of $(C_8-C_{20})$alkylbetaines, sulfobetaines, $(C_8-C_{20})$alkylamido-$(C_1-C_6)$alkylbetaines or $(C_8-C_{20})$alkylamido$(C_1-C_6)$alkylsulfobetaines.

Among the amine derivatives, mention may be made of the products sold under the name Miranol®, as described in U.S. Pat. Nos. 2,528,378 and 2,781,354 and having the structures:

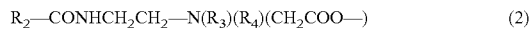

$$R_2\text{—CONHCH}_2\text{CH}_2\text{—N}(R_3)(R_4)(CH_2COO\text{—}) \quad (2)$$

in which: $R_2$ denotes an alkyl radical derived from an acid $R_2$—COOH present in hydrolyzed coconut oil, a heptyl, nonyl or undecyl radical, $R_3$ denotes a β-hydroxyethyl group and $R_4$ denotes a carboxymethyl group;

and

$$R_2\text{—CONHCH}_2\text{CH}_2\text{—N(B)(C)} \quad (3)$$

in which B represents —$CH_2CH_2OX'$, C represents —$(CH_2)_z$—Y', with z=1 or 2, X' denotes the —$CH_2CH_2$—COOH group or a hydrogen atom, Y' denotes —COOH or the —$CH_2$—CHOH—$SO_3H$ radical, $R_{2'}$ denotes an alkyl radical of an acid $R_9$—COOH present in coconut oil or in hydrolyzed linseed oil, an alkyl radical, especially of $C_7$, $C_9$, $C_{11}$ or $C_{13}$, a $C_{17}$ alkyl radical and its iso form, and an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caryloamphodipropionate, lauroamphodipropionic acid, cocoamphodipropionic acid.

By way of example, mention may be made of the cocoamphodiacetate sold under the trade name Miranol® C2M Concentrate by the company Rhodia.

The preferred amphoteric surfactants are alkylbetaines, alkylamidoalkylbetaines and coamphodiacetate.

More preferentially, the amphoteric surfactant is an alkylamidoalkylbetaine.

The composition according to the invention preferably comprises the amphoteric surfactant(s) in an amount ranging from 0.01% to 20% by weight and preferably from 5% to 15% by weight relative to the total weight of the composition.

The composition of the invention may also comprise nonionic surfactants, for example those described in the "Handbook of Surfactants" by M. R. Porter, published by Blackie & Son (Glasgow and London), 1991, pp. 116-178). Thus, they can be chosen in particular from polyethoxylated, polypropoxylated or polyglycerolated fatty acids, alkylphenols, alpha-diols or alcohols, having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$alkylamine oxides or N-acylaminopropylmorpholine oxides, preferably alkylpolyglycosides or oxyalkylenated fatty alcohols.

The dye composition in accordance with the invention may also contain one or more direct dyes that may be chosen especially from nitrobenzene dyes, azo direct dyes and methine direct dyes. These direct dyes may be of nonionic, anionic or cationic nature.

The medium that is suitable for dyeing, also known as the dye support, is generally constituted of water or of a mixture of water and of at least one organic solvent to dissolve the compounds that are not sufficiently water-soluble. Examples of organic solvents that may be mentioned include $C_1-C_4$ lower alkanols, such as ethanol and isopropanol; polyols and polyol ethers, for instance 2-butoxyethanol, propylene glycol, propylene glycol monomethyl ether, diethylene glycol monomethyl ether and monoethyl ether, and also aromatic alcohols, for instance benzyl alcohol or phenoxyethanol, and mixtures thereof.

For the dyeing of human keratin fibers, the dyeing medium is a suitable cosmetic medium.

The solvents may be present in proportions preferably of between 1% and 40% by weight approximately, and even more preferentially between 5% and 30% by weight approximately, relative to the total weight of the dye composition.

The dye composition in accordance with the invention may also contain various adjuvants conventionally used in hair dye compositions, such as anionic or zwitterionic surfactants or mixtures thereof, anionic, cationic, nonionic, amphoteric or zwitterionic polymers or mixtures thereof, thickeners other than the bioheterosaccharides that are useful in the present invention, antioxidants, penetrants, sequestrants, fragrances, buffers, dispersants, conditioning agents, for instance volatile or nonvolatile, modified or unmodified silicones, film-forming agents, ceramides, preserving agents and opacifiers.

These above adjuvants are generally present in an amount for each of them of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisioned addition(s).

The pH of the dye composition in accordance with the invention is generally between about 3 and 12 and preferably between about 5 and 11.

It may be adjusted to the desired value by means of acidifying or basifying agents usually used in the dyeing of keratin fibers, or alternatively by means of standard buffer systems.

Among the acidifying agents that may be mentioned, for example, are mineral or organic acids, for instance hydrochloric acid, orthophosphoric acid, sulfuric acid, carboxylic acids, for instance acetic acid, tartaric acid, citric acid and lactic acid, and sulfonic acids.

Among the basifying agents that may be mentioned, for example, are aqueous ammonia, alkali metal carbonates, alkanolamines such as monoethanolamine, diethanolamine and triethanolamine, and also derivatives thereof, sodium hydroxide, potassium hydroxide and the compounds of formula (III) below:

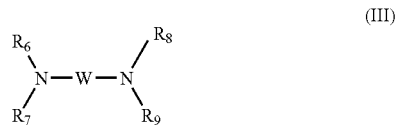

(III)

in which W is a propylene residue optionally substituted with a hydroxyl group or a $C_1$-$C_4$ alkyl radical; $R_6$, $R_7$, $R_8$ and $R_9$, which may be identical or different, represent a hydrogen atom or a $C_1$-$C_4$ alkyl or $C_1$-$C_4$ hydroxyalkyl radical.

The dye composition according to the invention may be in various forms, such as in the form of liquids, creams or gels, or in any other form that is suitable for dyeing keratin fibers, and especially human hair.

The process of the present invention is a process in which the composition according to the present invention as defined previously is applied to the fibers, in the presence of an oxidizing agent, for a time that is sufficient to develop the desired coloration. The color may be revealed at acidic, neutral or alkaline pH and the oxidizing agent may be added to the composition of the invention just at the time of use, or it may be used starting with an oxidizing composition containing it, applied simultaneously or sequentially to the composition of the invention.

According to one particular embodiment, the composition according to the present invention is mixed, preferably at the time of use, with a composition containing, in a medium that is suitable for dyeing, at least one oxidizing agent, this oxidizing agent being present in an amount that is sufficient to develop a coloration. The mixture obtained is then applied to the keratin fibers. After a leave-on time of from 3 to 50 minutes approximately and preferably 5 to 30 minutes approximately, the keratin fibers are rinsed, shampooed, rinsed again and then dried.

The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in hair dye compositions and as defined previously.

The pH of the oxidizing composition containing the oxidizing agent is such that, after mixing with the dye composition, the pH of the resulting composition applied to the keratin fibers preferably ranges between 3 and 12 approximately and even more preferentially between 5 and 11. It may be adjusted to the desired value by means of acidifying or basifying agents usually used in the dyeing of keratin fibers and as defined previously.

The ready-to-use composition that is finally applied to the keratin fibers may be in various forms, such as in the form of liquids, creams or gels or in any other form that is suitable for dyeing keratin fibers, and especially human hair.

A subject of the invention is also a multi-compartment device or dyeing "kit" in which a first compartment contains the dye composition of the present invention defined above and a second compartment contains an oxidizing agent. This device may be equipped with a means for applying the desired mixture to the hair, such as the devices described in patent FR 2 586 913 in the name of the Applicant.

Using this device, it is possible to dye the keratin fibers by means of a process that involves mixing a dye composition comprising at least one oxidation base of formula (I) with an oxidizing agent, and applying the mixture obtained to the keratin fibers for a time that is sufficient to develop the desired coloration.

EXAMPLES

The compositions below were prepared, the amounts indicated being, unless otherwise mentioned, weight amounts.

|  | Example | Example 2 |
|---|---|---|
| TOLUENE-2,5-DIAMINE | 0.3 | 0.64 |
| 2-METHYL-5-HYDROXYETHYLAMINOPHENOL | 0.1 |  |
| 2,4-DIAMINOPHENOXYETHANOL HCl |  | 0.01 |
| 4-AMINO-2-HYDROXYTOLUENE | 0.1 |  |
| 6-HYDROXYINDOLE | 0.027 |  |
| 2-AMINO-3-HYDROXYPYRIDINE | 0.2 |  |
| RESORCINOL | 0.05 | 0.66 |
| m-AMINOPHENOL | 0.01 | 0.085 |
| p-AMINOPHENOL | 0.27 |  |
| PENTASODIUM PENTETATE | 2 | 2 |
| AMMONIUM THIOLACTATE | 0.8 |  |
| AMMONIUM HYDROXIDE | 11.1 | 11.1 |
| SODIUM METABISULFITE |  | 0.71 |
| SCLEROTIUM GUM | 1 | 1 |
| AMODIMETHICONE (and) TRIDECETH-6 (and) CETRIMONIUM CHLORIDE | 1.8 | 1.8 |
| PROPYLENE GLYCOL | 2 |  |
| CETEARYL ALCOHOL | 7 | 7 |
| BEHENTRIMONIUM CHLORIDE | 4 | 4 |
| COCAMIDOPROPYL BETAINE | 10.53 | 10.53 |
| AQUA | qs | qs |

The above compositions are mixed with 20-volumes aqueous hydrogen peroxide solution (1 volume of composition per 1.5 volumes of oxidizing agent).

The mixture thus obtained is applied easily to locks of natural gray hair containing 90% white hairs. After a leave-on time of 30 minutes, the hair is rinsed, washed with a standard shampoo and dried.

The hair coloration is evaluated visually.

|  | Tone depth | Glint |
|---|---|---|
| Example 1 | Dark blond | Red |
| Example 2 | Dark blond | Natural |

The two shades obtained are sparingly selective.

For each of these examples, the same result is obtained when the 1% of sclerotium gum is replaced with 1% of xanthan gum.

The invention claimed is:

1. A composition for dyeing keratin fibers, comprising at least one dye precursor, at least one bioheteropolysaccharide, at least one cationic surfactant and at least one amphoteric surfactant;
wherein:
the at least one bioheteropolysaccharide is chosen from sclerotium gums;
the at least one amphoteric surfactant is chosen from betaines; and
the weight ratio of the at least one cationic surfactant to the at least one bioheteropolysaccharide is greater than 1.

2. The composition according to claim 1, wherein the at least one dye precursor is chosen from oxidation bases and couplers.

3. The composition according to claim 2, wherein the at least one dye precursor is at least one oxidation base chosen from para-phenylenediamines, bis(phenyl)alkylenediamines, para-aminophenols, bis-para-aminophenols, ortho-aminophenols, heterocyclic bases, and the addition salts thereof.

4. The composition according to claim 2, wherein the at least one dye precursor is at least one coupler chosen from meta-phenylenediamines, meta-aminophenols, meta-diphenols, naphthalene-based couplers, heterocyclic couplers, and the addition salts thereof.

5. The composition according to claim 1, wherein the at least one dye precursor comprises at least one oxidation base and at least one coupler.

6. The composition according to claim 1, wherein the at least one dye precursor is at least one oxidation base and/or at least one coupler; and
further wherein:
the at least one oxidation base is present in an amount ranging from 0.001% to 10% by weight, relative to the total weight of the composition; and
the at least one coupler, when present, is present in an amount ranging from 0.001% to 10% by weight, relative to the total weight of the composition.

7. The composition according to claim 1, wherein the at least one bioheteropolysaccharide is present in an amount ranging from 0.01% to 10% by weight, relative to the total weight of the composition.

8. The composition according to claim 7, wherein the at least one bioheteropolysaccharide is present in an amount ranging from 0.1% to 4% by weight, relative to the total weight of the composition.

9. The composition according to claim 1, wherein the at least one cationic surfactant is chosen from primary, secondary, or tertiary fatty amine salts and quaternary ammonium salts, and mixtures thereof.

10. The composition according to claim 9, wherein the at least one cationic surfactant is chosen from behenyltrimethylammonium chloride, cetyltrimethylammonium chloride, quaternium-83, quaternium-87, behenylamidopropyl-2,3-dihydroxypropyldimethylammonium chloride, palmitylamidopropyltrimethylammonium chloride and stearamido-propyldimethylamine.

11. The composition according to claim 1, wherein the at least one cationic surfactant is present in an amount ranging from 0.01% to 10% by weight, relative to the total weight of the composition.

12. The composition according to claim 11, wherein the at least one cationic surfactant is present in an amount ranging from 0.1% to 4% by weight, relative to the total weight of the composition.

13. The composition according to claim 1, further comprising at least one nonionic surfactant chosen from alkylpolyglycosides and oxyalkylenated fatty alcohols.

14. The composition according to claim 1, wherein the at least one amphoteric surfactant is chosen from alkylbetaines and alkylamidoalkylbetaines.

15. The composition according to claim 1, wherein the at least one amphoteric surfactant is present in an amount ranging from 0.01% to 20% by weight, relative to the total weight of the composition.

16. The composition according to claim 15, wherein the at least one amphoteric surfactant is present in an amount ranging from 5% to 15% by weight, relative to the total weight of the composition.

17. The composition according to claim 1, further comprising at least one direct dye.

18. A process for dyeing keratin fibers, comprising:
applying to the keratin fibers, in the presence of at least one oxidizing agent, at least one composition for dyeing keratin fibers, comprising at least one dye precursor, at least one bioheteropolysaccharide, at least one cationic surfactant, and at least one amphoteric surfactant;
wherein:
the at least one bioheteropolysaccharide is chosen from sclerotium gums;
the at least one amphoteric surfactant is chosen from betaines; and
the weight ratio of the at least one cationic surfactant to the at least one bioheteropolysaccharide is greater than 1; and
leaving the at least one composition on the keratin fibers for a period of time sufficient to develop a desired coloration.

19. A multi-compartment device, comprising:
a first compartment containing at least one composition for dyeing keratin fibers, comprising at least one dye precursor, at least one bioheteropolysaccharide, at least one cationic surfactant, and at least one amphoteric surfactant;
wherein:
the at least one bioheteropolysaccharide is chosen from sclerotium gums;
the at least one amphoteric surfactant is chosen from betaines; and
the weight ratio of the at least one cationic surfactant to the at least one bioheteropolysaccharide is greater than 1; and
a second compartment containing at least one oxidizing agent.

* * * * *